United States Patent [19]

Barber

[11] Patent Number: 4,928,677
[45] Date of Patent: May 29, 1990

[54] HYGIENE SPLINT

[75] Inventor: Lois M. Barber, Pismo Beach, Calif.

[73] Assignee: LMB Hand Rehab Products, San Luis Obispo, Calif.

[21] Appl. No.: 309,115

[22] Filed: Feb. 13, 1989

[51] Int. Cl.[5] .............................................. A61F 5/00
[52] U.S. Cl. ................................ 128/87 R; 128/89 R; 128/87 A; 2/11
[58] Field of Search ................ 128/92 R, 87 A, 87 R, 128/77; 2/11, 16, 20

[56] References Cited

U.S. PATENT DOCUMENTS

| 896,674 | 8/1908 | Walker | 128/89 R |
|---|---|---|---|
| 1,174,675 | 3/1916 | Cady | 128/87 A |
| 1,177,398 | 3/1916 | Dorang | 128/87 A |
| 1,313,344 | 8/1919 | Smart | 128/87 R |
| 1,328,598 | 1/1920 | Schilling | 128/87 A |
| 1,867,258 | 7/1932 | Fruehauf | 128/87 A |
| 2,312,523 | 3/1943 | Corbett | 128/87 A |
| 2,318,864 | 5/1943 | Jackson | 128/87 A |
| 3,036,831 | 8/1960 | Engan | 2/16 |
| 3,408,077 | 10/1968 | Norwood | 128/87 R |
| 4,190,902 | 3/1980 | Rhee | 128/87 R X |
| 4,287,609 | 9/1981 | Amadeo | 2/16 |

Primary Examiner—Robert A. Hafer
Assistant Examiner—Lynda M. Cofsky
Attorney, Agent, or Firm—George F. Bethel; Patience K. Bethel

[57] ABSTRACT

A hygiene splint for supporting the wrist and forearm and holding the fingers in an extended position, including a hand grip extending transversely-across the palm, a hand and wrist support adapted to contact the ulnar and ventral side of the hand, a forearm support having a generally triangular configuration for contact with the underside of the forearm. A soft moisture absorbent strap encloses the hand grip and is wrapped several times around the hand and forearm prior to securement. Foam slip-on tubes of increasing diameter can be slipped over the hand grip to gradually open contracted fingers.

17 Claims, 3 Drawing Sheets

HYGIENE SPLINT

BACKGROUND OF THE INVENTION

1. Field of the Invention

This invention relates to the field of hand splints and especially to a hygiene splint which holds the wrist out of the flexion position and holds the fingers in the extended position.

2. Description of the Prior Art

In recent years various hand splints combining soft materials of foam and wire have been provided which are more comfortable and adjustable for the correction of problems than the wood and plaster splints used in the past. These foam and wire hand splints are advantageous in that they are flexible and individually adjustable to enable the gradual urging of bones back into the normal position. This permits adjustments to allow for swelling and/or pain. Each splint must be designed to correct the particular problem which is experienced by the patient.

Patients under long-term care, especially older patients frequently experience a painful condition of the hand which is often the result of poor positioning over long periods of time or the result of brain injury or stroke. Such conditions produce muscle contractures resulting in a flexed wrist and fingers which are tightly clenched into the palm. In extremes cases, this can result in a maceration of the skin in the palm of the hand. The fingers become paralyzed in this position resulting in secondary problems. Among the most important problems is the hygiene of the hand. It is almost impossible to properly cleanse the hand when in a tightly clenched position.

It is an object of this invention to provide a hygiene splint which will hold the fingers out of the palm and support the wrist in a comfortable position. Another object is to permit functioning of the fingers.

It is an object of this invention to provide a splint design which increases ventilation, is easily put on and removed and also incorporates washability, durability, and light weight as well as comfort.

It is also an object of the invention to provide cushioning for light weight and comfort, to prevent pressure problems and provide for exposure to the air to minimize perspiration. Moreover, it is desirable, in this particular case, to provide a splint which is sufficiently soft to prevent self-injury by the patient. Finally, it is an object of this invention to provide a specialized splint which is designed to correct and treat flexion of the wrist and muscle contractures of the fingers.

SUMMARY OF THE INVENTION

The hygiene splint of the invention is particularly designed to hold the wrist out of the flexed position and at the same time hold the fingers in an extended position. By another embodiment the splint provides functionality to the fingers.

The splint includes a hand grip, attached to a wrist support which is attached to a generally open triangular forearm section. The splint has a framework of wire sandwiched in a layer of cushioning foam.

The hygiene splint of the invention contacts the palm transversely in the form of a hand grip. The portion of the hand grip which contacts the ulnar side of the palm extends at an angle downwardly along the ulnar side of the palm to the wrist. Here there is a division into two legs, one leg extending outwardly along the ulnar side of the forearm and the other leg extending outwardly along the radial side of the arm. The entire splint is enclosed in a sandwich of foam. Substantially all of the areas lying between the forearm leg extensions are left open and free of foam to improve ventilation. Fastening means are attached to the forearm leg section.

The hand grip is provided with one or more slip-on tubes of foam of varying diameter which are employed for the gradual opening of the fingers.

The hand grip with or without the foam tube is covered with a fabric sleeve of considerable length which is used to secure the splint to the hand and wrist by wrapping. One advantage of the fabric covering is that it can be easily put on and removed. Also, it is especially desirable because it can be washed to provide hygienic conditions during the wearing of the splint.

In addition, the outer foam covering of the splint can be washed with soap and water.

The malleable wire framework of the splint provides individual adjustment by manual bending. This allows for individual fitting as well as for subsequent adjustments required as the splint exerts its force to provide the desired correction.

The soft fabric cover, the cushioned foam covering, and the absence of sharp or protruding portions are designed to avoid self-injury by the patient.

Another advantage of the splint is that it can be used on a left or right hand by turning it over. If desired the splint can be used as the basis for the attachment of a variety of additions to the hand grip such as a finger platform, a thumb support, and the like.

Preferably the fabric covering is made of a cotton material which will absorb perspiration, is washable and capable of being sterilized.

While the splint is provided with varying diameter foam tubes which overlie the hand grip, the splint can be used without the foam slip-on tubes or cylinders when only wrist correction is needed with only minor finger support.

The splint is designed to contact the ventral side of the hand, wrist and forearm. Only the strapping material contacts the dorsal part of the hand, wrist and forearm.

The splint framework can be formed from one continuous unbroken length of wire. This makes possible a minimum of interior joining pieces, and a minimum of sharp edges which could cause protrusions through the exterior foam covering.

A particular feature of the invention is that the splint provides an opening for the thenar eminence of the thumb.

As used herein and in the appended claims: "Volar" refers to the palm or underside of the forearm or hand; "Dorsal" refers to the back of the hand or forearm; "Ventral" refers to the underside of the hand or forearm; "Radial" refers to the side of the hand and forearm on the side of the thumb; "Ulnar" refers to the side of the hand and forearm on the side of the little finger; "IP" refers to interphalangeal; "MP" refers to metacarpophalangeal; "CM" refers to carpometacarpal; "PIP" refers to proximal interphalangeal; "DIP" refers to distal interphalangeal; "Distal" means farthest from the center of the body; "Proximal" means closest to the center of the body; "Thenar eminence" refers to the bulge at the base of the thumb; and, "Carpus" refers to the wrist.

The fabric covering or sleeve which also functions as the fastening strap is wrapped several times completely around the hand, wrist and forearm as well as the splint. It is secured within a pair of D-shaped loops providing ease in attachment and detachment of the splint. The strapping also allows for the adjustment and distribution of pressure along the hand and forearm while at the same time preventing slipping of the splint on the hand. The hygiene splint of the invention provides excellent ventilation due to its open design.

If additional wear resistance is required in addition to the foam padding, an additional layer of abrasion resistant sheeting such as leather or vinyl can be adhered to the cushioning material without departing from the spirit of the invention.

BRIEF DESCRIPTION OF THE DRAWINGS

The invention will be more clearly understood by reference to the description below, taken in conjunction with the accompanying drawings wherein.

DETAILED DESCRIPTION OF THE INVENTION

Figure 1:
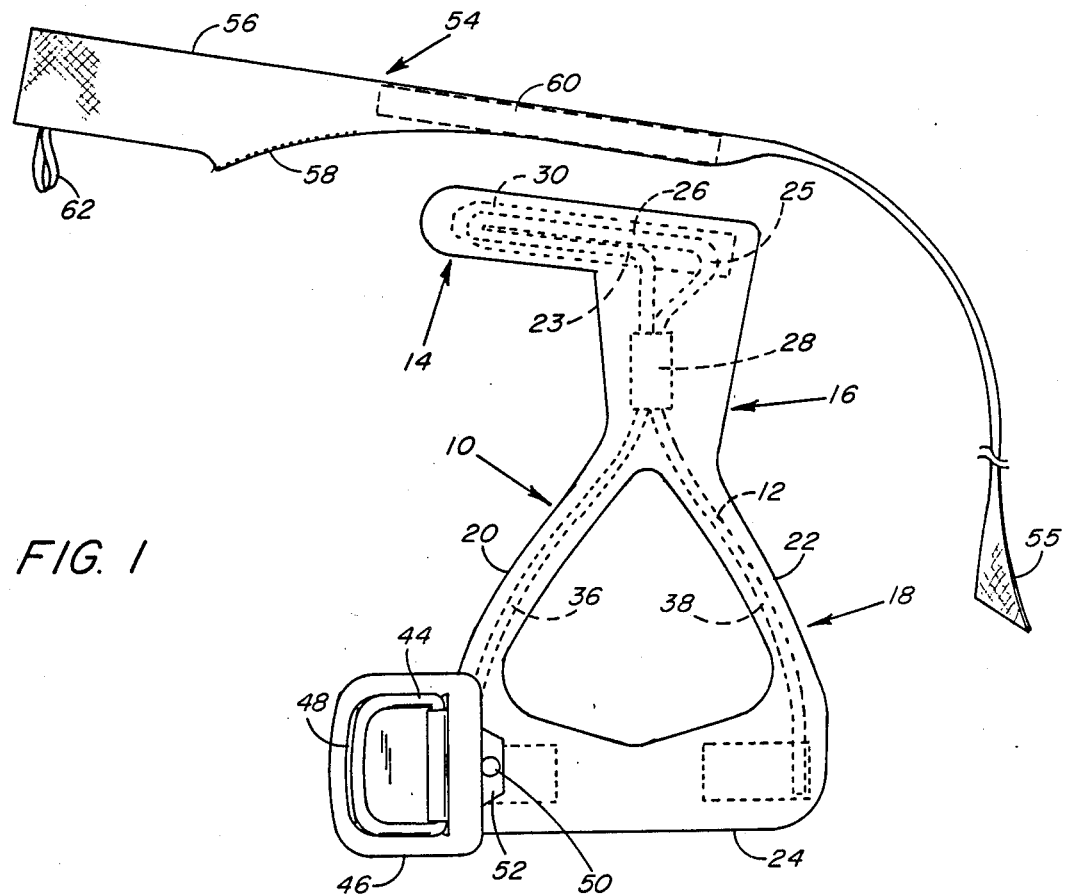
FIG. 1 shows a plan view of the hygiene splint of the invention with the cushioned fabric strap removed therefrom.

A left hand hygiene splint designated 10 is shown in FIG. 1 with the wire framework 12 shown in outline. The same splint can be used for the right hand simply by turning it over. The hygiene splint includes a hand grip 14 in the form of a bar which is connected to a wrist support 16 which is disposed on the ventral and ulnar side of the palm and wrist. The function of the hand grip 14 is to hold the fingers out of the palm. By contacting only the ventral and ulnar side of the palm and wrist, the wrist support 16 provides support to the wrist while leaving the thumb and thenar eminence free from contact. This permits freedom of movement to the thumb allowing limited use of the hand.

The wrist support 16 divides or diverges into a generally open triangular forearm support 18 which is in contact with the ventral or underside of the forearm. The generally triangular forearm piece 18 includes legs 20 and 22 and a flexible base 24. This can be seen with greater particularity in FIGS. 4 and 5.

Figure 6:
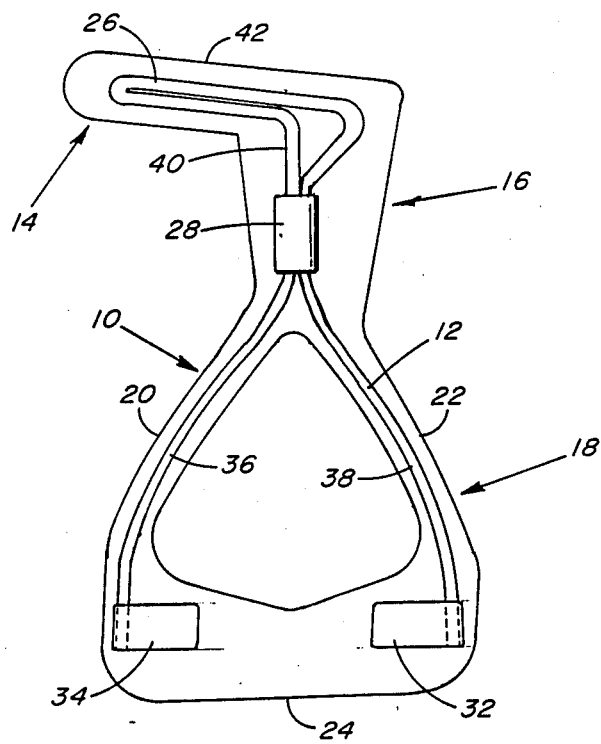
FIG. 6 shows the splint of the invention with one layer of foam removed to show the outline of the framework of the splint.

The framework of the splint 12 is shown in outline in FIG. 1 and in greater detail in FIG. 6 which shows a portion of the splint removed to give a view of the framework.

As shown in FIG. 6, the framework 12 includes a single length of bendable wire which is bent to provide a hand grip support framework 26. The framework 26 includes a shorter section of wire 23 and a longer section of wire 25. The shorter wire 23 is bent substantially at a right angle to its length and the longer wire 25 is bent at about a 45° angle to its length. The two wires are held together in a necked down area 40 which is held by a vinyl tube 28 to provide support for the wrist area. The necked down area 40 extends outwardly to provide two legs 36 and 38 in a generally arched configuration. Wire 36 extends from wire 23 and wire 38 extends from wire 25. The end of wire 36 has a piece of preferably aluminum or other malleable sheeting 34 crimped around the end. In the same manner, leg 38 has a piece of preferably aluminum sheeting 32 crimped around its end.

As can be seen in outline in FIG. 1, the hand grip support framework 26 is enclosed in a sleeve of rubber tubing 30 shown in outline in FIG. 1.

The splint as described is enclosed in a sandwich of foamed material 42 which is preferably heat-sealed along the edges. A flexible bridge or base 24 of foam spans the distance between the respective framework legs 36 and 38.

The flexible base 24 of the forearm piece 18 is provided with a pair of D-rings 44 and 48 which rest on a piece of vinyl 46. The D-rings 44 and 48 are secured to the splint 10 by means of a rivet 50 which secures the D-rings 44 and 48 by means of a piece of vinyl 52 which encloses one end of the base 24. This can be seen especially in FIGS. 1 and 2. The rivet passes through the vinyl strip 52, the outer foam covering 42 of the splint 10, the aluminum sheet 34, another outer layer of foam 42 and finally the other side of the vinyl strip 52.

Figure 4:
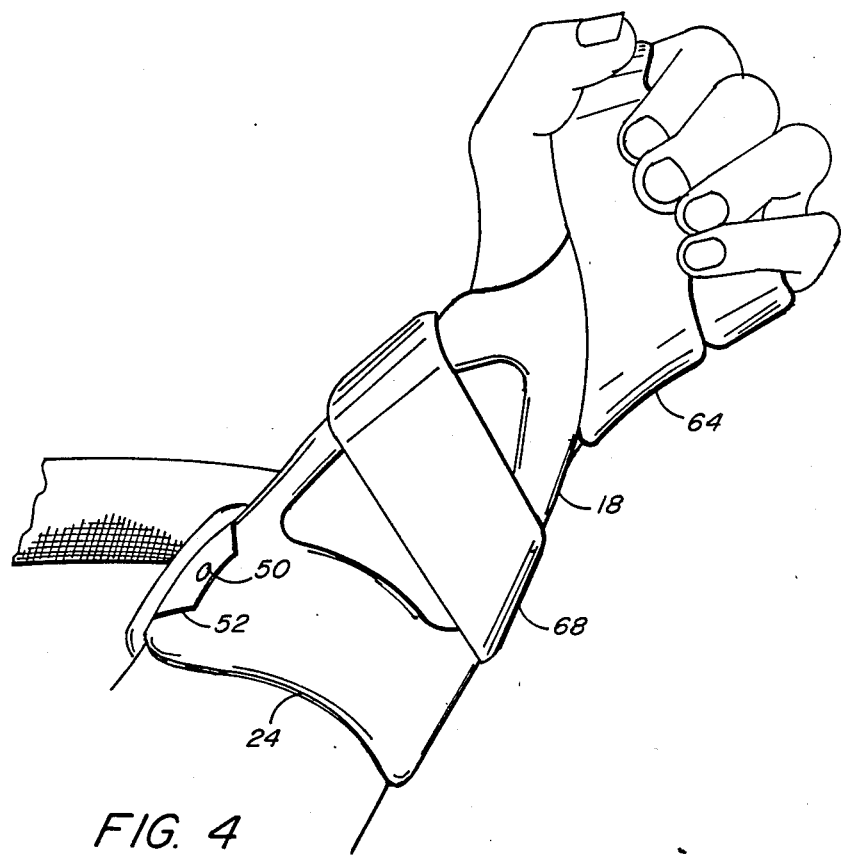
FIG. 4 shows a perspective view of the ventral side of the hand and forearm with the splint in place and the fabric strap partially wrapped around the forearm.

As can be seen in the view shown in FIG. 4, the flexible base 24 of the hygiene splint 10 conforms to the curve of the underside of the forearm. This is made possible because there is no wire reinforcement in this particular area as can be seen in FIGS. 1 and 6. This not only permits increased comfort but also better fit. It also enables the splint to be made in a size which is sufficient to accommodate varying sized hands and forearms.

It can also be seen that the splint can be reversed so that it can be used for a left hand or for a right hand. This is also made possible by the flexible unreinforced base 24 of the splint.

The strap 54 of the splint is unique. It is shown in a partially broken away view in FIG. 1. The strap 54 has an overall generally tubular configuration. It includes a sleeve member 56 at one end which is designed to slip over the hand grip 14 of the splint 10. The sleeve opening is indicated at 58 for insertion of the hand grip 14.

Figure 5:
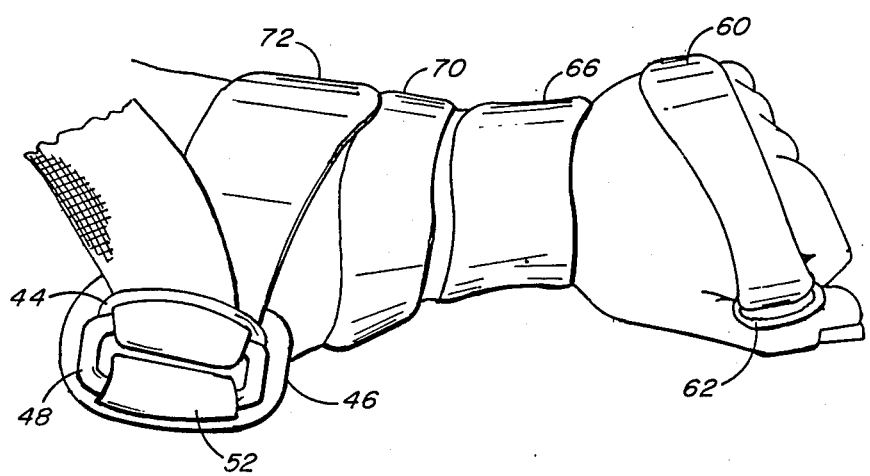
FIG. 5 shows a perspective view of the dorsal and radial side of the hand and forearm with the splint in place and the fabric strapping in place.

Adjacent to the sleeve opening 58 is a padded area 60 shown in outline in FIG. 1. The padded area consists of a piece of foam which is secured within the strap 54. As can be seen in FIG. 5, the padded area 60 is positioned to cushion and cover the back of the hand.

The strap 54 also includes a loop 62 substantially at the end of the sleeve portion 56. When in use, after contacting the back of the hand the free end 55 of the strap 54 is inserted within the loop 62 as shown in FIG. 5. The strap 54 is then brought diagonally across the palm of a user and splint 10 as indicated in FIG. 4 at 64. The strap 54 then passes over the back of the wrist of a user as shown in FIG. 5 and as indicated at 66. The strap 54 extends again diagonally across the forearm piece 18 as indicated at 68. It continues diagonally across the dorsal forearm as indicated at 70. The strap 54 passes another time around the ventral forearm (not shown) and extends across the dorsal forearm as indicated at 72 where the free end 55 is secured within D-rings 44 and 48 to provide an adjustable tension.

In the above described manner the hygiene splint provides support to the fingers, wrist, and forearm by a strapping method which is adjustable, soft, and suited to varying sized hands.

Figure 2:
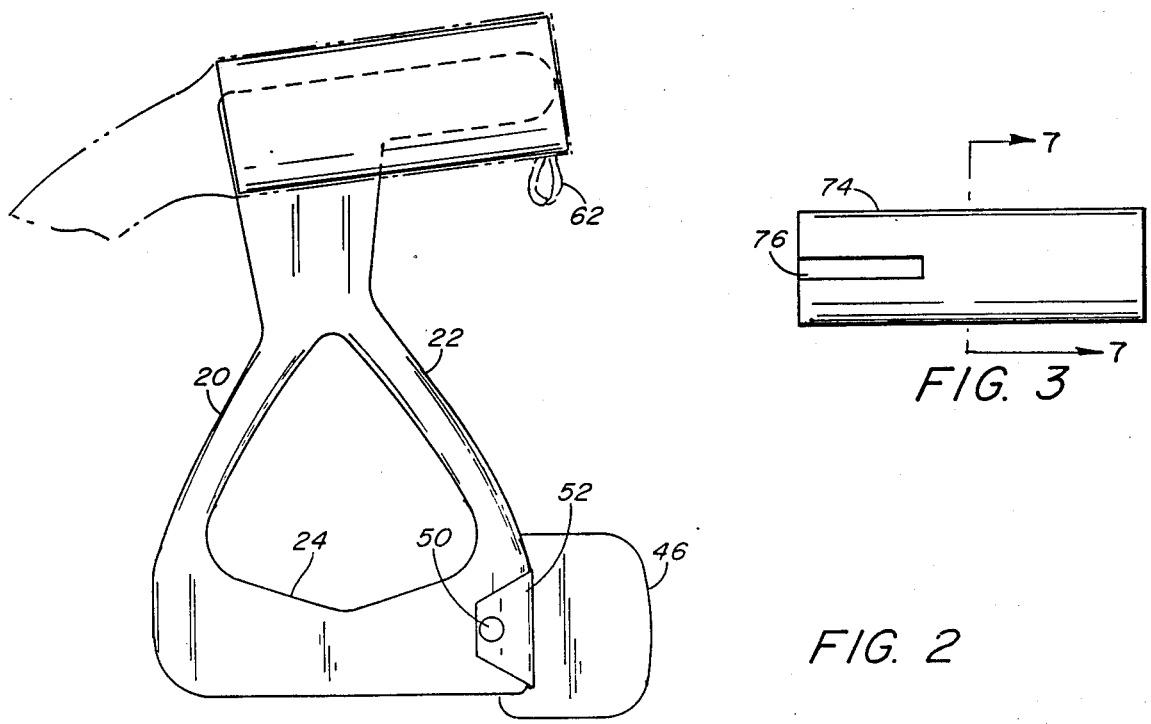
FIG. 2 shows the reverse plan view of the splint of FIG. 1 with a foam slip-on tube and with the fabric covering partially broken away.
Figure 3:
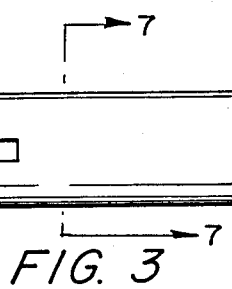
FIG. 3 shows the slip-on foam tube for the hand grip.
Figure 7:
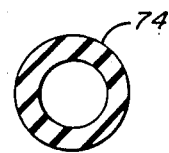
FIG. 7 shows a cross section of the slip-on foam tube for the hand grip taken along the lines 7—7 of FIG. 3.

The embodiment shown in FIG. 2 incorporates a slip-on tubular foam member 74 as shown in FIGS. 2, 3, and 7. As shown, the tubular member 74 includes a slot 76. The tubular member 74 slip fits over the hand grip 14. The slot 76 accommodates the width of the wrist support area 16.

In the same manner as for the splint shown in FIGS. 4 and 5, the splint 10 with the slip-on tubular foam member 74 is also provided with a sleeve-like strapping material 54. The sleeve portion 56 is slightly enlarged to accommodate the size of the tubular member 74 but in other respects remains the same. The wrapping is exactly the same as described for FIGS. 4 and 5.

The provision of the tubular member 74 permits the gradual increase in diameter by use of tubular members of varying diameter to gradually open clenched fingers over a period of time.

One of the features of the hygiene splint of the invention is that the thenar eminence of the thumb is not encumbered. This permits freedom of movement to the thumb. Moreover, the open design which minimally contacts the hand, wrist and forearm increases ventilation and avoids perspiration.

The materials of which the splint are constructed permit individual adjustment of the splint without requiring special tools. While the preferred support material for the framework is an aluminum wire because of its light weight, low cost, and malleable characteristics, other types of metals can be substituted therefore. Such metals should be light weight, reinforcing metals which provide the strength and malleable characteristics of aluminum, such as, for example, among others, copper, steel, brass, and the like.

In place of metal, there could also be used a malleable type of plastic such as a malleable, resilient type of natural or synthetic rubber or a metal reinforced plastic.

The splint 10 is enclosed preferably in a sandwich of pliant cushioning material, preferably a heat-sealable polyethylene foam or equivalent material. Preferably, such cushioning material is water proof and provides sufficient cushioning of the framework of the splint.

Other types of foam can also be used, such as, for example, polypropylene foam, ionomer foam, polystyrene foam, polyurethane foam, PVC (polyvinylchloride) flexible foam, and silicone foam. The above mentioned plastic foams are intended to be exemplary. They are not intended in any way to limit the type of cushioning material which can be used in the invention. Not all of the above mentioned foams are capable of being heat-sealed and might require adhesive to improve the bonding of the foam layers. This should in no way limit the use thereof.

The main advantages of the use of polyethylene foam include the characteristics of low water absorption, good energy absorption, water vapor barrier, compressibility, smooth surface, thermal stability at temperatures up to 215° F. and a high ratio of tensile and shear strength compared to other resilient foams. In addition, the capability of being heat-sealed also makes it additionally attractive.

While a nylon sleeve 28 is used to hold the respective framework wires together in the splint of the invention, other types of plastic and other materials can be substituted. For example, the tube 28 can be replaced by one or more layers of tape or a metal clip or ring.

While a rubber tubing 30 encloses the framework wires 23 and 25 of the hand grip 14, other soft materials can be used as well. For example, the wires 26 can be wrapped with a foam tape to provide substantially the same characteristics.

With respect to the strap 54, it is preferably comprised of cotton or other soft, washable material which can be sterilized. Obviously, various types of synthetic fibers made into fabrics alone or in combination with natural fibers as cotton, linen and wool can also be used.

The strap is preferably made in a tubular manner with an opening as shown in the drawings but it will be obvious that the strap can be sewn to provide substantially the same result.

Also, while the strap 54 has been provided with a cushioned area 60, for overlying the back of the hand, the entire strapping material can be provided with cushioning if desired without departing from the spirit and scope of the invention.

Although the strap is shown to be secured by means of the D-rings 44 and 48, other securement means can also be used such as, for example, buckles or combinations of brushed material with patches of small plastic hooks. Other types of securement means including snaps, buttons, hooks, and the like can also be used. However, these materials are not as preferred.

While the strapping is shown to be encircling the hand and forearm with four wraps, fewer and greater numbers can be utilized under certain circumstances. Four wraps is preferred as shown in the drawings as it provides the ideal support needed for the wrist and forearm.

It should also be mentioned that the splint of the invention can be made in differing sizes with respect to length as well as width without departing from the invention. While a left hand splint is shown in the drawings, the right hand splint constitutes the reverse, since the same splint can be used for a left or right hand. This is one of the advantages of the splint.

Various modifications of the invention are contemplated and can be resorted to by those skilled in the art without departing from the spirit and scope of the invention as defined by the following claims.

I claim:

1. A hygiene splint useable for a right hand or a left hand by turning the splint over comprising:
    a hand grip for holding the fingers out of the palm of a user;
    a ventral wrist support adapted to contact the ulnar side of a wrist and palm of a user and adapted to leave the thumb and thenar eminence substantially free from contact;
    a ventral forearm support for support of said forearm;
    means joining said hand grip, said ventral wrist support, and said ventral forearm support;
    said means joining said hand grip, said ventral wrist support and said ventral forearm support comprising at least one wire which extends from said hand grip to said ventral wrist support and from said ventral wrist support to said ventral forearm support;
    strap means for securing said splint to the hand, wrist, and forearm of a user;

a manually bendable support framework with a pliant cushioning material enclosing at least a portion of said framework; and wherein:

said framework is formed of a continuous unbroken length of malleable wire.

2. A splint as claimed in claim 1 wherein said continuous length of wire is bent at substantially its midpoint to provide two substantially parallel wires adapted to extend transversely across the palm of a user to form the hand grip framework, which wires are further bent to generally follow the ventral and ulnar side of the hand of a user to form said wrist support while avoiding contact with the thumb and thenar eminence wherein said forearm support framework is formed by said wires diverging outwardly from said wrist support to provide a generally wishbone configuration.

3. A splint as claimed in claim 2, said wishbone configuration comprising said forearm framework support having two respective free ends of said wires;

one leg of said wishbone configuration generally following the ulnar side of the forearm and the other leg of the wishbone configuration generally following the radial side of the forearm; and, wherein said framework is at least partially enclosed by a sandwich of pliant cushioning material which leaves a portion of the diverging area between the wires substantially free of cushioning material so that a substantial portion of the ventral forearm of a user is not contacted by the splint, and at the same time said foam providing a bridge portion of pliant cushioning material extending between the ends of said wishbone configuration which is adapted to provide a soft, flexible transverse section to said ventral forearm support piece which conforms to the curvature of the forearm of a user.

4. A splint as claimed in claim 3 further comprising a slip-on tube of cushioning material for enlarging the diameter of said hand grip.

5. A splint as claimed in claim 3 wherein said strap means comprises a length of soft fabric including enclosing means at one end for enclosing said hand grip and a free end having a length sufficiently long to permit wrapping several times around said splint when implaced upon the hand and forearm of a user and further comprising means attached to said forearm piece for securing the end of said strapping means.

6. A splint as claimed in claim 5 wherein said strapping means further comprises a loop disposed near the end of said enclosing means; and, a cushioned section within said strap for placement over the back of a hand during wrapping and wherein said means for attachment of said strapping means includes a pair of D-rings secured to one end of said flexible transverse section of said ventral forearm support.

7. A splint as claimed in claim 6 wherein said strapping material is formed of a washable, moisture absorbent, material and wherein said strapping material after enclosing said hand grip is inserted within said loop so that said cushioning material lies across the dorsal hand of a user and is then passed between the thumb and the index finger and is further wrapped at least once around the dorsal forearm of a user prior to being secured to said D-rings.

8. A manually adjustable hygiene splint useable for a right hand or a left hand by turning the splint over for holding the fingers out of the palm and supporting the wrist and forearm of a user comprising:

a transverse finger support having two end regions and adapted to contact the fingers and palm of a user transversely for support of the fingers of a user;

a hand and wrist support extending from one end region of said finger support and adapted to contact the ulnar and ventral side of the hand and wrist of a user while leaving the thumb and thenar eminence of a user substantially free from contact;

a ventral forearm support which extends from said hand and wrist support by diverging into two legs, one leg of which is adapted to contact the ulnar side of the forearm of a user and the other leg of which is adapted to contact the radial side of the forearm of a user and including a flexible member which unites the ends of said legs and is adapted to contact and conform to a portion of the forearm of a user;

said splint including an interior framework of malleable wire supporting substantially all of said splint except said flexible member;

said splint being at least partially enclosed in a sandwich of soft cushioning foam and having a strap securement means attached to said flexible member; and, strap means in the form of a length of soft, washable material having an opening for enclosing at least a portion of said finger support and having a length sufficiently long and a width sufficiently narrow to permit several wraps around the splint when implaced upon a user and be held by said strap securement means.

9. A hygiene splint as claimed in claim 8 wherein said finger support is comprised of a framework of two wires covered with at least one layer of soft cushioning foam adapted to receive removable slip-on foam tubes of increasing diameter to gradually open the fingers of a user.

10. A hygiene splint as claimed in claim 9 wherein said finger support wires are of unequal length and said hand and wrist support is formed by an extension of said two wires of said finger support, and further comprising holding means within said hand and wrist framework to hold said wires in juxtaposition.

11. A hygiene splint as claimed in claim 10 wherein said ventral forearm support framework is formed by an extension of said two wires of said hand and wrist support, and, said wires extending in a diverging manner from said holding means to provide two legs of substantially bowed configuration.

12. A hygiene splint as claimed in claim 11 wherein said legs of said ventral forearm support are separately enclosed in cushioning foam and wherein said flexible member comprises a section of foam uniting the ends of each leg for transverse contact with the ventral forearm of a user.

13. A hygiene splint as claimed in claim 12 wherein said strap means comprises a tube of washable absorbent material, having an opening at one end for enclosing said finger support, and any slip-on foam tube, and including a cushioned pad for overlying the dorsal hand of a user.

14. A hygiene splint as claimed in claim 13 wherein said strap includes a loop on the enclosing end of said strap for receiving said strap.

15. A hygiene splint as claimed in claim 14 wherein said hygiene splint is secured to the hand of a user by enclosing said finger support with said strap, and extending said cushioned part of said strap over the dorsal hand of a user, passing through said loop and across the palm of a user leaving the thumb free from the strap then extending across the hand and wrist support around the dorsal wrist of a user across the forearm support, across the ventral forearm to be secured by said strap securement means.

16. A hygiene splint as claimed in claim 15 wherein said wire framework is formed of aluminum and wherein said strap is made of cotton.

17. A hygiene splint as claimed in claim 8 further comprising at least one removable piece selected from a finger platform and a thumb support.

* * * * *